(12) United States Patent
Chen

(10) Patent No.: US 6,987,133 B2
(45) Date of Patent: Jan. 17, 2006

(54) TOPICAL SPRAY FOR BURN TREATMENT AND ANTI-INFECTION

(75) Inventor: Jivn-Ren Chen, Shreveport, LA (US)

(73) Assignee: Sage Pharmaceuticals, Inc., Shreveport, LA (US)

( * ) Notice: Subject to any disclaimer, the term of this patent is extended or adjusted under 35 U.S.C. 154(b) by 0 days.

(21) Appl. No.: 10/404,801

(22) Filed: Apr. 1, 2003

(65) Prior Publication Data

US 2003/0170182 A1    Sep. 11, 2003

Related U.S. Application Data

(60) Division of application No. 09/338,363, filed on Jun. 23, 1999, now Pat. No. 6,551,577, which is a continuation of application No. PCT/US98/09753, filed on May 12, 1998.

(60) Provisional application No. 60/046,287, filed on May 12, 1997.

(51) Int. Cl.
*A61K 47/32* (2006.01)
*A01N 25/34* (2006.01)
*A01N 43/54* (2006.01)

(52) U.S. Cl. .................. 514/772.4; 424/404; 514/256
(58) Field of Classification Search ............... 514/886
See application file for complete search history.

(56) References Cited

U.S. PATENT DOCUMENTS

| 4,431,637 A | * | 2/1984 | Upeslacis et al. | ............. 514/25 |
| 4,670,592 A | * | 6/1987 | Eakin et al. | ................ 564/234 |
| 5,747,058 A | * | 5/1998 | Tipton et al. | ............... 424/423 |
| 5,905,092 A | * | 5/1999 | Osborne et al. | ......... 514/772.4 |

* cited by examiner

*Primary Examiner*—Thurman K. Page
*Assistant Examiner*—Retford Berko
(74) *Attorney, Agent, or Firm*—Jackson Walker L.L.P.

(57) ABSTRACT

This invention relates to a topical spray preparation for burn treatment and microbial infections on human being or animals. This non-aerosol preparation contains an antimicrobial drug, i.e., silver sulfadiazine, as is dispersed or solubilized in a cream or lotion base matrix which can be sprayed directly from a common trigger spray device. The key component of the matrix can be characterized by it having a suitable molecular weight polymer of cross-linked acrylic acid, such as Carbomers or non-ionic surfactants such as polyoxyethylene alkyl ethers, or any combination of the above materials.

12 Claims, No Drawings

TOPICAL SPRAY FOR BURN TREATMENT AND ANTI-INFECTION

This is a divisional application of prior U.S. patent application Ser. No. 09/338,363 filed Jun. 23, 1999 U.S. Pat. No. 6,551,577, which is a continuation of PCT/US98/09753, filed 12 May 1998, claiming the priority of U.S. Provisional Application No. 60/046,287, filed May 12, 1997, the content of which are incorporated by reference into this application.

Throughout this application, various references are referred to throughout the application. Disclosures of these publications in their entireties are hereby incorporated by reference into this application to more fully describe the state of the art to which this invention pertains.

BACKGROUND OF THE INVENTION

This invention relates to a topical spray preparation for burn treatment and microbial infections on human being or animals. This non-aerosol preparation contains an antimicrobial drug, i.e., silver sulfadiazine, as is dispersed or solubilized in a cream or lotion base matrix which can be sprayed directly from a common trigger spray device. The key component of the matrix can be characterized by it having a suitable molecular weight polymer of cross-linked acrylic acid, such as Carbomers or non-ionic surfactants such as polyoxyethylene alkyl ethers, or any combination of the above materials.

A wound may be defined as a defect or break in the skin that outcomes from physical, mechanical or thermal damage including burns. There are several different types of burns: thermal, chemical, electrical, and those caused by radiation. Deep dermal (second degree) and full thickness (third degree) burns, in which most of the protective epithelium layer and almost all of the element of the skin are destroyed, can rapidly acquire bacteria and cause infection. Infection in the burn wound is the most common management problem in the care of the burn patient. The infection in a major burn could, if untreated, can rapidly develop into a life-threatening septicaemia.

Silver sulfadiazine was first described in 1943 by Wruble (M. Wruble, J. Am. Pharm. Ass. 32, 80, 1943) and was found to be mildly antiseptic. Fox (Ch. L. Fox, Arch. Surg. 96, 184, 1968) rejuvenated the compound for the topical treatment of burns. The 1% w/w of this active drug, in its cream form, has been in clinical use in the U.S.A. since 1973. It is one of only two approved active drugs used as a topical antibacterial agent for adjunctive therapy in second and third degree burns.

U.S. Pat. No. 3,761,590 describes a process for preparing a thick cream ointment containing silver sulfadiazine which is useful in burn treatment. It has been clinically well known that silver sulfadiazine is effective against a wide variety of gram-positive and gram-negative organisms, including *Pseudomonas* and *Candida*. However, the activity of the silver sulfadiazine, in the cream form, may be influenced by the following key factors: (1) the release rate of active from the cream matrix in the wound environment; (2) particle size and solubility of the active drug in the fluids of the wound bed; and (3) stability of the active in the cream matrix. In addition, the cream product contains poor water soluble fat and oil materials, making it mandatory that the treated area must be cleaned and the cream must be removed from the wounded area, which is time consuming and excruciatingly painful.

Presently, these cream base products can only be applied using only sterile techniques. Again, the task of this kind of drug administration is extremely time consuming and can allow for potential cross-contamination between patients due to the multiple use of the same container. The latter reason usually restrains the practitioner to prescribe this product to the patient, and to be used only in the clinical setting, not at home after each treatment. Therefore, the patient has to return to the burn center for a new application of the cream, even if the burn is minor. Accordingly, there is a definite desperate need in the art for developing an economical, less painful, easy to apply, clean, and cross-contamination free formulation for a burn and antibacterial treatment.

U.S. Pat. No. 5,143,717 presents a specific aerosol formulation of an antibiotic including silver sulfadiazine in a cream base as a topical water soluble foam. This invention provides several advantageous features over the presently marketed formulations while minimizing the disadvantages thereof. However, there are four key points related to this invention that need to be clarified: (1) The manufacturing process requires special equipment for product aerosolization. (2) This aerosol product requires the interior of an aerosol can to be lined or have a protective coating in order to stabilize the active silver compound. (3) The possible chilling effect on the sensitive wound area may impact the patient when sprayed. (4) The foam, when in contact with the patient, does not adhere to the wound area and it easily slides off, and the concentration of the antimicrobial agent at that location of treatment is diminished, and the addition of dressings are unable to properly cover and hold the antimicrobial foam in place. The currently marketed product instructions require the patient to have total coverage and contact of the product with the damaged site at all times.

U.S. Pat. No. 4,803,066 teaches a topical preparation comprises a synergistic mixture of an antimicrobial silver compound and an antimicrobial azole compound in hydrophilic and hydrophobic ointment, tablet, pessary and aqueous gel. This invention describes a number of suitable gelling agents including polyoxyethylene-polyoxypropylene diol block copolymers (poloxamer) and no technology about the aqueous gel for trigger spray has been mentioned.

This block copolymers are known as gelling agents for a substantial amount of time. U.S. Pat. No. 3,639,575 accomplishes the invention by the use of certain polyoxyethylene polyoxypropylene block copolymers (poloxamer) as a matrix for silver ions in the preparation of aqueous gel compositions.

U.S. Pat. No. 4,551,139 discloses an apparatus and method for spray application of a silver sulfadiazine cream to treat the burn. The cream is pushed toward an outlet in a collapsible bag, in which the cream is disposed by means of pressure applied to the exterior surface of the bag, and conveying the cream from the outlet to a sanitary spray nozzle by means of a compressed air operated sanitary pump. This is a complex system in terms of the manufacturing process and practical clinical application. This invention did not reveal the formulation of the specific high viscosity cream.

SUMMARY OF THE INVENTION

Accordingly, the purpose of the present invention is to provide a non-aerosol sprayable topical dosage form for the burn treatment and antimicrobial therapy for human being and animals, and to equip all the superior advantageous features over the presently used formulations while minimizing the disadvantages thereof. The advantages are, but not limited to the following:

(1) easier application to the burn area;
(2) cooling sensation to minimize the pain;
(3) suitable active drug releasing rate from the cream matrix;
(4) easier washing;
(5) high stability of active drug; and
(6) suitable efficacy and safety product.

The further object of the present invention is to use pharmaceutical acceptable ingredients to manufacture a non-aerosol spray cream, lotion or gel in a common trigger spray container. These formulations do not require propellants, high pressure and a special aerosol can.

The foregoing and additional objects are attained by providing a specific non-aerosol sprayable formulation of an antimicrobial agent or combination of antimicrobial agents dispersed or solubilized in a cream, lotion or gel that contains pharmaceutical polymers or non-ionic surfactant(s), humectant, preservatives and purified water.

Another object of this invention is to disclose a non-heating manufacturing processes for this non-aerosol sprayable cream, lotion or gel and the common trigger spray packaging device for this cream, lotion or gel.

DETAILED DESCRIPTION OF THE INVENTION

This is an invention of an improved pharmaceutical dosage form for topical application to treat the burn wound and infections. This dosage form introduces an unprecedented application method for antimicrobial agent without propellants and high pressure in the container. The cream, lotion or gel packaged in a common trigger spray container will be firmly adhered to the burn or wound area as a regular cream does after it is sprayed out from the container. This dosage form can demonstrate tremendous advantages in the clinical application over the current marketed products in terms of financial aspects, as well as compliances both to practitioner and patient. The antimicrobial effect of silver sulfadiazine and chlorhexidine compounds have been clinically established. There are a great number of inventions using silver sulfadiazine as an antimicrobial agent in dosage forms, as well as in a variety of medical devices, but none so far has mentioned it in the non-aerosol spray cream, lotion or gel form. Chlorhexidine is a bisbiguanide antiseptic and disinfectant effective against a wide range of bacteria, some fungi and some viruses. It is used clinically in various preparations for various disinfecting purposes.

U.S. Pat. No. 4,803,066 teaches a topical preparation comprises synergistic mixture of an antimicrobial silver compound and an antimicrobial azole compound to achieve synergistic antibacterial and antifungal effect. Accordingly, in one aspect, the present invention provides a pharmaceutical non-aerosol spray composition for topical application which comprises silver or zinc sulfadiazine or chlorhexidine salt selected from the group of hydrochloride, digluconate or acetate as antimicrobial agents. It can be used alone or in any combination. The silver or zinc sulfadiazine in the micronized form is present in an amount in the range of 0.5 to 5% by weight, and chlorhexidine salt is present in an amount in the range of 0.05 to 10% by weight of cream, lotion or gel.

The antimicrobial agent or agents used in the present invention can be incorporated into a neutral hydrophilic matrix cream, lotion or gel. In a first preferred embodiment, the cream or lotion matrix for burn treatment and anti-infection is characterized by a polyoxyethylene alkyl ethers. In a second preferred embodiment, the burn treatment and antimicrobial gel is characterized by high molecular weight polymer of cross-linked acrylic acid (Carbomer). Polyoxyethylene alkyl ethers are non-ionic surfactants widely used in pharmaceutical topical formulations and cosmetics primarily as emulsifying agents for water-in-oil and oil-in-water emulsions. It is characterized in this invention as a base for non-aerosol trigger sprayable cream or lotion. Cross-linked acrylic acid polymer (Carbomer) employed to form the gel is an another object of this invention.

A particularly suitable base for non-aerosol spray is therefore a cream or lotion containing from 1 to 25% of polyoxyethylene alkyl ethers, 3 to 40% of humectant and 0.1 to 1% of preservative or preservatives and the balance to 100% being purified water. Aptly the polyoxyethylene alkyl ether can be one or any combination selected from the group consisting of polyoxyl 20 cetostearyl ether (Atlas G-3713), poloxyl 2 cetyl ether (ceteth-2), poloxyl 10 cetyl ether (ceteth-10), poloxyl 20 cetyl ether (ceteth-20), poloxyl 4 lauryl cetyl ether (laureth-4), poloxyl 23 lauryl cetyl ether (laureth-23), poloxyl 2 oleyl ether (oleth-2) poloxyl 10 oleyl ether (oleth-10), poloxyl 20 oleyl ether (oleth-20), poloxyl 2 stearyl ether (steareth-2), poloxyl 10 stearyl ether (steareth-10), poloxyl 20 stearyl ether (steareth-20) and poloxyl 100 stearyl ether (steareth-100). Suitable humectant can be one or any combination selected from the group consisting of propylene glycol, polyethylene glycol, sorbitol or glycerine. Suitable preservative is one or any combination selected from the group consisting of methylparaben, propylparaben, benzyl alcohol, benzoic acid, sodium benzoate, sorbic acid and its salt or phenylethyl alcohol.

Another suitable base for non-aerosol spray is a gel containing from 0.1 to 2.0% of Carbomer, 0.1 to 1% of alkaline solution, 3 to 40% of humectant and 0.1 to 1% of preservative or preservative as and the balance to 100% being purified water. Aptly the Carbomer can be one or any combination selected from the group consisting of Carbomer 934, Carbomer 940 or Carbomer 941. The suitable humectant, preservative and purified water for the gel are same as that in the case or cream or lotion.

This invention is demonstrated in detail with the following working examples and experiments which however should not limit this invention.

EXAMPLES AND EXPERIMENTS

Example 1

Gel Formulation:

| | |
|---|---|
| Silver sulfadiazine, micronized | 100 Gm. |
| Carbomer 934 | 30 Gm. |
| Propylene glycol | 400 mL. |
| Strong ammonia solution | 40 mL. |
| Methylparaben | 30 Gm. |
| Purified water, USP q.s. to | 10,000 Gm. |

Disperse the Carbomer uniformly in about 40% of total amount of water. Add the ammonia solution gradually into the dispersion with agitation, a clear gel is formed. In a separate container dissolve the methylparaben in propylene glycol and then disperse the micronized silver sulfadiazine in this solution to form a homogeneous suspension. Gradually add the suspension into the gel with agitation, an uniform white opaque gel will be obtained.

Example 2

Cream or Lotion Formulation:

| | |
|---|---|
| Silver sulfadiazine, micronized | 100 Gm. |
| Poloxyl 2 cetyl ether | 500 Gm. |
| Propylene glycol | 500 mL. |
| Methylparaben | 30 Gm. |
| Purified water, USP q.s. to | 10,000 Gm. |

Dissolve the methylparaben in about 80% of total amount of propylene glycol. Add the poloxyl 2 cetyl ether into this solution with agitation. In a separate processing container mix the 20% of the total amount of propylene glycol and part of purified water, and disperse the micronized silver sulfadiazine in the mixture to form an uniform suspension. Gradually add suspension into the first processing container with agitation until a homogeneous, soft, white cream is obtained. Pass the cream through a colloid mill and bring the mass of the batch up to the targeted quantity.

Example 3

Trigger Spray Container:

The trigger spray device for packaging the gel in Example 1 or cream or lotion in Example 2 is the T S-800 Trigger Spray manufactured by Calmar Dispensing Systems (Watchung, N.J., U.S.A.). It is designed to spray an 8 inch diameter pattern when set on the spray setting and sprayed from a distance of 8 inches. The same sprayer will spray in a 2 inch diameter pattern when set on the stream setting and sprayed from a distance of 8 inches.

Experiment 1

Product Stability:

The product of Example 2 packaged in Example 3 has performed a stability study to evaluate its expiration date. The spray head is actuated to let the cream fill in the tube and spray head prior to be placed in the stability station.

Stability data are obtained from the actuated sample bottles stored at accelerated condition of 40° C. for at least 3 months; at intensive light condition of ambient room temperature (ART) for 1 month and at ambient room temperature for up to 36 months. The results conclude that both physical and chemical data show that the product remains stable for 36 months upon storage at the ART condition. The statistic method of regression line and exponential curve for 95% confidence limit has been used for data analysis. The result from accelerated condition (40° C.) supports the two years tentative expiration date for this product. The result from an actual long term ART (20° C.–25° C.) condition further demonstrates that this product can actual have a 36 month expiration date.

Experiment 2

Antimicrobial Zonal Inhition Assay:

An anticrobial potency test of non-aerosol spray cream from Example 2 was conducted to compare with that of leading commercial cream product. The antimicrobial zonal inhibition assay was employed in this test. The student's t-test was performed to compare the antimicrobial potency of the two products against each strain of the bacteria. The difference was considered significant when $p<0.05$.

The result of the test shows that the antimicrobial potency of non-aerosol spray cream is equivalent to that of leading commercial cream product, based on the zonal inhibition assay against *E. coli*, *Staphlococcus aureus*, *Enterococcus (Streptococcus) faecalis* and *Micrococcus leteus*.

Experiment 3

Bioequivalent and Acceptance Study:

A randomized, two-site, double-blind, parallel-group clinical study was conducted to compare the bioequivalence of non-aerosol sprayable cream of Example 2 (cream A) and commercial leading cream product (cream B) and to evaluate the physical characteristics and patient/practitioner acceptance of cream A.

For post-treatment investigator evaluation overall data, cream A was evaluated as being more washable than cream B ($p=0.0450$). At one site, the former was evaluated as both more washable ($p=0.0167$) and more spreadable ($p=0.0255$) than latter.

For patient/nurse subjective evaluation, overall data cream B was evaluated as more easily applied than cream A at the fourth ($p=0.0393$) and fifth ($p=0.0490$) applications. Similar results were noted at one site for the fourth ($p=0.0020$) and fifth ($p=0.0268$) applications, as well as when all six application evaluations were averaged ($p=0.0265$).

At one site, cream A was evaluated as more easily removed than cream B when all six removal evaluations were averaged ($p=0.0089$).

At one site, cream A evaluated as having a cooler sensation than cream B at the fourth application ($p=0.0170$), and when all six application evaluations were averaged ($p=0.0404$). Near-significant results were noted for cream A in the overall data at the fourth application ($p=0.0503$), and when all application evaluations were averaged ($p=0.0743$).

For laboratory overall data, patients using cream A had a statistically lower serum sulfadiazine post-treatment level ($p=0.0485$). A near-significant result ($p=0.0524$) was noted for patients using cream A at one site. There were no significant differences between the treatment groups for urine silver or sulfadiazine concentrations. The results for wound bacterial count did not show any significant differences for either treatment group.

Results of this study conclude that:

(1) cream A is bioequivalent to cream B. Investigator evaluations of treatment response, infection control, equivalence, wound appearance and overall evaluation did not reveal any significant differences between the two treatments. Likewise, statistical analysis of microbial testing of wound cultures did not produce any significant differences between the treatments; and (2) in the patient/practitioner acceptance evaluations, cream B was rated superior to cream A only in ease of application, while cream A was rated superior to cream B for washability, ease of removal and patient perception of wound temperature change.

What is claimed is:

1. A method of treating burns, wounds and other topical infections of human being or animal hosts comprising spraying a non-aerosol spray system onto a disorder area, wherein the non-aerosol spray system comprises:

(a) a hand or finger trigger sprayable hydrophilic matrix composition; wherein the hydrophilic matrix composition comprises:
  (i) a bisbiguanide salt or a micronized sulfanilamide salt;
  (ii) about 0.1 to about 25% of a hydrophilic base, wherein the hydrophilic base is about 0.1 to about 2% of cross-linked acrylic acid polymer or polymers with about 0.1 to about 2% of alkaline solution or about 1 to about 25% of polyoxyethylene alkyl ether or ethers, wherein the cross-linked acrylic acid polymer is Carbomer 934, Carbomer 940, or Carbomer 941, wherein the alkaline solution is about 25% of sodium hydroxide solution or strong ammonia solution;
  (iii) about 3 to about 40% of a humectant;
  (iv) about 0.1 to about 1% of a preservative; and
  (v) suitable amount of purified water to adjust to 100%; and
(b) a hand or finger trigger actuated pump spray device designed to spray a wide or narrow spray pattern.

2. A method of treating burns, wounds and other topical infections of human being or animal hosts comprising pouring a non-aerosol spray system onto a disorder area, wherein the non-aerosol spray system comprises:
(a) a hand or finger trigger sprayable hydrophilic matrix composition; wherein the hydrophilic matrix composition comprises:
  (i) a bisbiguanide salt or a micronized sulfanilamide salt;
  (ii) about 0.1 to about 25% of a hydrophilic base, wherein the hydrophilic base is about 0.1 to about 2% of cross-linked acrylic acid polymer or polymers with about 0.1 to about 2% of alkaline solution or about 1 to about 25% of polyoxyethylene alkyl ether or ethers, wherein the cross-linked acrylic acid polymer is Carbomer 934, Carbomer 940, or Carbomer 941, wherein the alkaline solution is about 25% of sodium hydroxide solution or strong ammonia solution;
  (iii) about 3 to about 40% of a humectant;
  (iv) about 0.1 to about 1% of a preservative; and
  (v) suitable amount of purified water to adjust to 100%; and
(b) a hand or finger trigger actuated pump spray device designed to spray a wide or narrow spray pattern; and
wherein the hand or finger trigger actuated pump spray device is removed prior to pouring.

3. The method of claim 1, wherein the polyoxyethylene alkyl ether is selected from the group consisting of poloxyl 20 cetostearyl ether, poloxyl 2 cetyl ether, poloxyl 10 cetyl ether, poloxyl 20 cetyl ether, poloxyl 4 lauryl cetyl ether, poloxyl 23 lauryl cetyl ether, poloxyl 2 oleyl ether, poloxyl 10 oleyl ether, poloxyl 20 oleyl ether, poloxyl 2 stearyl ether, poloxyl 10 stearyl ether, poloxyl 20 stearyl ether and poloxyl 100 stearyl ether.

4. The method of claim 1, wherein the humectant or humectants are selected from the group consisting of propylene glycol, polyethylene glycol, sorbitol and glycerine.

5. The method of claim 1, wherein the preservative or preservatives are selected from the group consisting of methylparaben, propylparaben, benzyl alcohol, benzoic acid, sodium benzoate, potassium benzoate, sorbic acid, sodium sorbate, potassium sorbate and phenylethyl alcohol.

6. The composition prepared by the method of claim 1.

7. The method of claim 2, wherein the polyoxyethylene alkyl ether is selected from the group consisting of poloxyl 20 cetostearyl ether, poloxyl 2 cetyl ether, poloxyl 10 cetyl ether, poloxyl 20 cetyl ether, poloxyl 4 lauryl cetyl ether, poloxyl 23 lauryl cetyl ether, poloxyl 2 oleyl ether, poloxyl 10 oleyl ether, poloxyl 20 oleyl ether, poloxyl 2 stearyl ether, poloxyl 10 stearyl ether, poloxyl 20 stearyl ether and poloxyl 100 stearyl ether.

8. The method of claim 2, wherein the humectant or humectants are selected from the group consisting of propylene glycol, polyethylene glycol, sorbitol and glycerine.

9. The method of claim 2, wherein the preservative or preservatives are selected from the group consisting of methylparaben, propylparaben, benzyl alcohol, benzoic acid, sodium benzoate, potassium benzoate, sorbic acid, sodium sorbate, potassium sorbate and phenylethyl alcohol.

10. A non-aerosol spray system for burn treatment and anti-infection on a human being or an animal comprises:
(a) a hand or finger trigger sprayable hydrophilic matrix composition, wherein the hydrophilic matrix composition comprises chlorhexidine salts or micronized sulfadiazine salts; and
(b) a hand or finger trigger actuated pump spray device designed to spray a wide or narrow spray pattern.

11. A non-aerosol spray system for burn treatment and anti-infection on a human being or an animal comprises:
(a) a hand or finger trigger sprayable hydrophilic matrix composition, wherein the hydrophilic matrix composition comprises an antimicrobial agent, wherein the antimicrobial agent is:
  (i) a hydrochloride, a digluconate, or an acetate salt of bisbiguanide salt in an amount in the range of about 0.05 to about 10% by weight of the hydrophilic matrix; or
  (ii) a micronized silver or a zinc salt of sulfanilamide in an amount in the range of about 0.5 to about 5% by weight of the hydrophilic matrix; and
(b) a hand or finger trigger actuated pump spray device designed to spray a wide or narrow spray pattern.

12. A non-aerosol spray system for burn treatment and anti-infection on a human being or an animal comprises:
(a) a hand or finger trigger sprayable hydrophilic matrix composition; wherein the hydrophilic matrix composition comprises:
  (i) a bisbiguanide salt or a micronized sulfanilamide salt;
  (ii) about 0.1 to about 25% of a hydrophilic base;
  (iii) about 3 to about 40% of a humectant;
  (iv) about 0.1 to about 1% of a preservative; and
  (v) suitable amount of purified water to adjust to 100%; and
(b) a hand or finger trigger actuated pump spray device designed to spray a wide or narrow spray pattern.

* * * * *